United States Patent
Pekarske et al.

(10) Patent No.: US 12,381,642 B2
(45) Date of Patent: Aug. 5, 2025

(54) SETTING AND DYNAMICALLY ADJUSTING A HYSTERESIS VALUE USED TO CONTROL ROAMING OF A WIRELESS MONITORING SYSTEM

(71) Applicant: GE Precision Healthcare LLC, Wauwatosa, WI (US)

(72) Inventors: Matthew Richard Pekarske, Grafton, WI (US); Tuomas Valtteri Laine, Vantaa (FI)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 880 days.

(21) Appl. No.: 17/646,258

(22) Filed: Dec. 28, 2021

(65) Prior Publication Data
US 2023/0208538 A1   Jun. 29, 2023

(51) Int. Cl.
*H04B 17/318* (2015.01)
*A61B 5/00* (2006.01)
*H04L 67/12* (2022.01)
*H04W 48/20* (2009.01)
*H04W 84/12* (2009.01)

(52) U.S. Cl.
CPC ......... *H04B 17/318* (2015.01); *A61B 5/0002* (2013.01); *H04L 67/12* (2013.01); *H04W 48/20* (2013.01); *H04W 84/12* (2013.01)

(58) Field of Classification Search
CPC .. H04B 17/318; H04B 17/328; A61B 5/0002; H04L 67/12; H04L 67/125; H04L 67/01; H04L 67/104; H04L 67/52; H04L 12/2803; H04W 84/18; H04W 84/12; H04W 48/20
See application file for complete search history.

(56) References Cited

U.S. PATENT DOCUMENTS

| | | | |
|---|---|---|---|
| 9,426,724 B2 | 8/2016 | Parron et al. | |
| 11,223,564 B2 | 1/2022 | Indiresan et al. | |
| 2004/0266474 A1* | 12/2004 | Petrus | H04B 17/382 455/524 |
| 2010/0303040 A1* | 12/2010 | Takamune | H04W 48/16 370/331 |
| 2020/0021996 A1* | 1/2020 | Harrod | H04W 16/10 |

OTHER PUBLICATIONS

Pekarske, M. et al., "Methods and Systems for Conditional Scanning," U.S. Appl. No. 17/648,269, filed Jan. 18, 2022, 35 pages.

* cited by examiner

*Primary Examiner* — Brian T Le
(74) *Attorney, Agent, or Firm* — McCoy Russell LLP

(57) ABSTRACT

Various methods and systems are provided for setting and dynamically adjusting a hysteresis value used to control roaming of a wireless monitoring system. The method for the wireless monitoring system comprises roaming to an access point (AP) based on a received signal strength indicator (RSSI) of a candidate AP relative to a hysteresis threshold and adjusting the hysteresis threshold responsive to a rate of change of an RSSI of a connected AP.

18 Claims, 4 Drawing Sheets

SETTING AND DYNAMICALLY ADJUSTING A HYSTERESIS VALUE USED TO CONTROL ROAMING OF A WIRELESS MONITORING SYSTEM

FIELD

Embodiments of the subject matter disclosed herein relate to wireless patient monitoring systems.

BACKGROUND

Wireless network systems may be used in retail, industry, medicine, manufacturing, and other enterprise environments to transmit and receive information among elements of a wireless network. For example, handheld devices may be wirelessly connected to a network via a plurality of access points (AP) of the wireless network system. Information such as inventory, machine availability, part manufacturing progress, and so on may be transmitted from the handheld device to the network via APs such that information input or stored on the handheld device may be accessed by other devices connected to the network. As the handheld devices move about a physical space of the wireless network system, a signal strength between an AP currently connected to the handheld device and the handheld device may change, for example, as the handheld device moves closer to or further from the currently connected AP. The signal strength may affect a speed of information transmission, energy used for transmission, and a time between information transmission by the handheld device and information receipt by the network.

In a hospital or other medical setting, monitoring of a patient's physiological information may be done in part using mobile patient monitors. The patient monitors may monitor patients as the patients, and therefore the patient monitors, move about a space such as the patients' room or the hospital. The patient monitors may be connected to at least one of a plurality of APs. The plurality of APs are connected to a network, which may further include a patient information database and/or other devices by which medical professionals may access and monitor patient data.

As the patient and therefore patient monitors move about a space, an available wireless signal strength may change. Devices in a healthcare setting may roam when stationary, due to changing environment (e.g., Wi-Fi Infrastructure events such as channel or power level changes, and/or a room door opening or closing), or when the patient monitor is mobile. Stationary roaming events may occur on the order of a few an hour whereas mobile events may occur once per 30 seconds for a duration of 15 minutes several times a day when the patient monitor is mobile, for example, when the patient walks a lap around the ward or goes to the cafeteria. Stationary and mobile roaming events may allow the patient monitor to disconnect from a currently connected AP and connect to a candidate AP in the space which may have a stronger wireless signal, thus allowing for continued transmission of information from the patient monitor to the network when the patient monitor is mobile or during environmental changes.

BRIEF DESCRIPTION

In one embodiment, a method comprises roaming to an access point (AP) in a medical facility based on a received signal strength indicator (RSSI) relative to the hysteresis threshold and adjusting the hysteresis threshold responsive to a rate of change of the RSSI.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be further explained in the following description of non-limiting embodiments, with reference to the attached drawings, wherein below.

DETAILED DESCRIPTION

Figure 2:
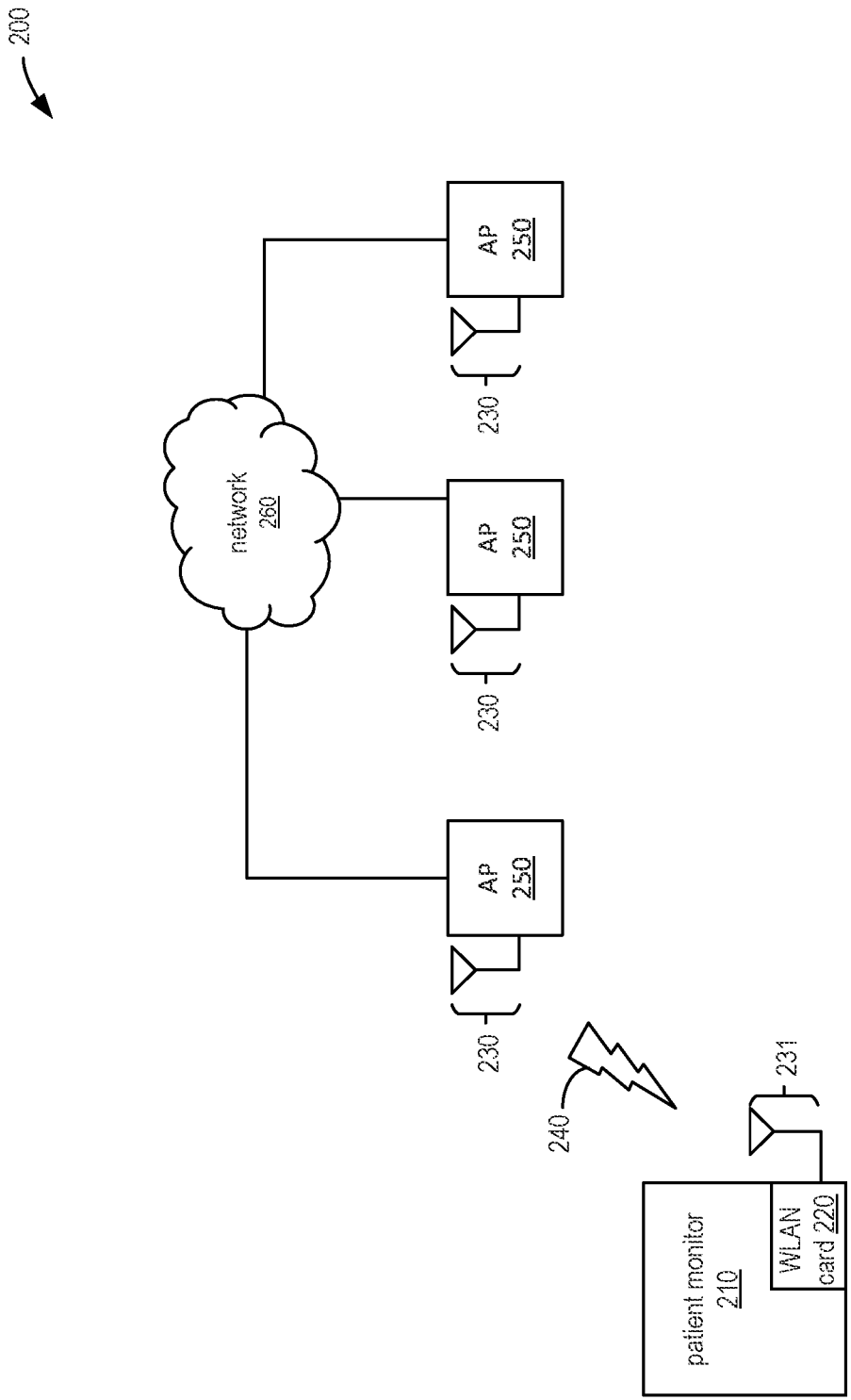
FIG. 2 shows a schematic block diagram illustrating communication of a patient monitor with a plurality of access points (APs).

The following description relates to various embodiments of a method and systems for dynamic setting and adjustment of a hysteresis value using information available to a patient monitor, herein also referred to as a Wi-Fi station (STA). A wireless system, as shown in FIG. 2, includes at least one patient monitor and a plurality of access points (APs). The APs are connected to a network and may be in wireless communication with the patient monitor via wireless transmission. The patient monitor may include a WLAN wireless card, which may store and execute computer executable code. For example, the code may include a method for dynamic setting and adjustment of a hysteresis value, comprising roaming to an AP in a medical facility based on a received signal strength indicator (RSSI) relative to the hysteresis threshold and adjusting the hysteresis threshold responsive to a rate of change of the RSSI.

Figure 3:
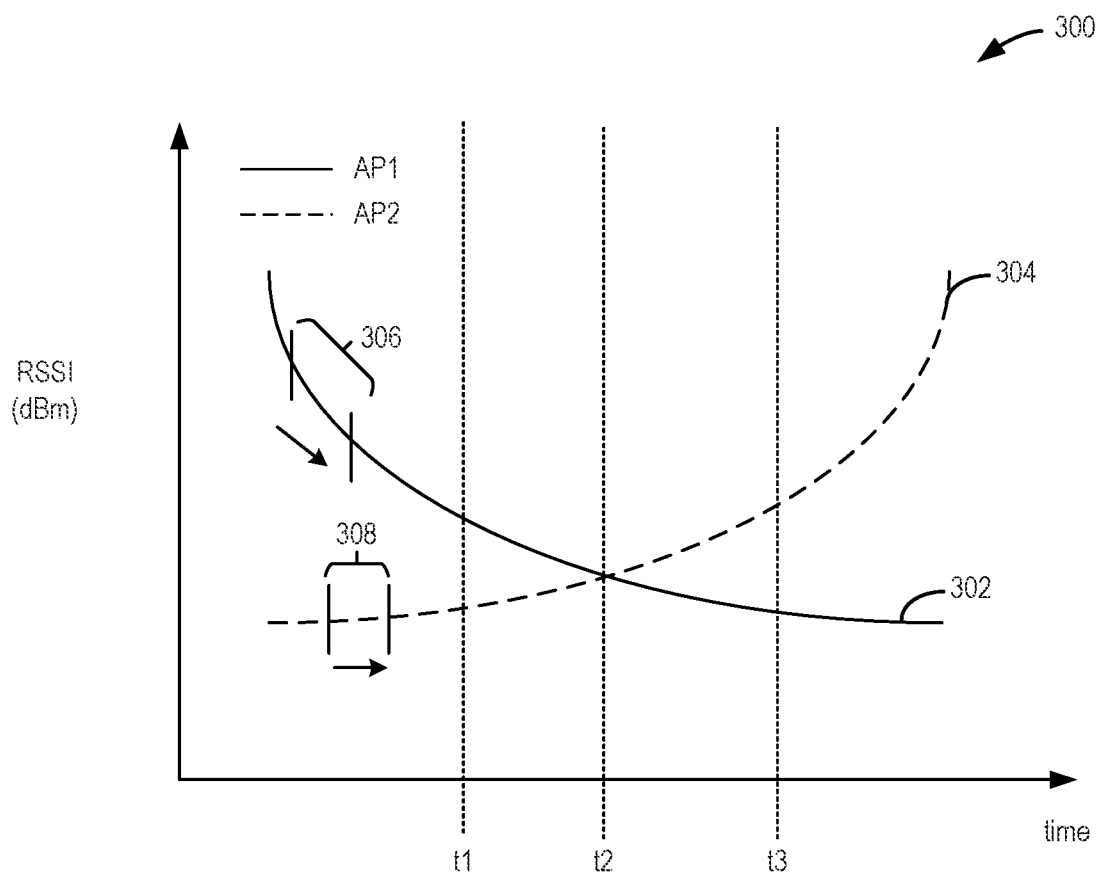
FIG. 3 shows a plot comparing a received signal strength indicator (RSSI) rate of change for a first AP and a second AP.
Figure 4:
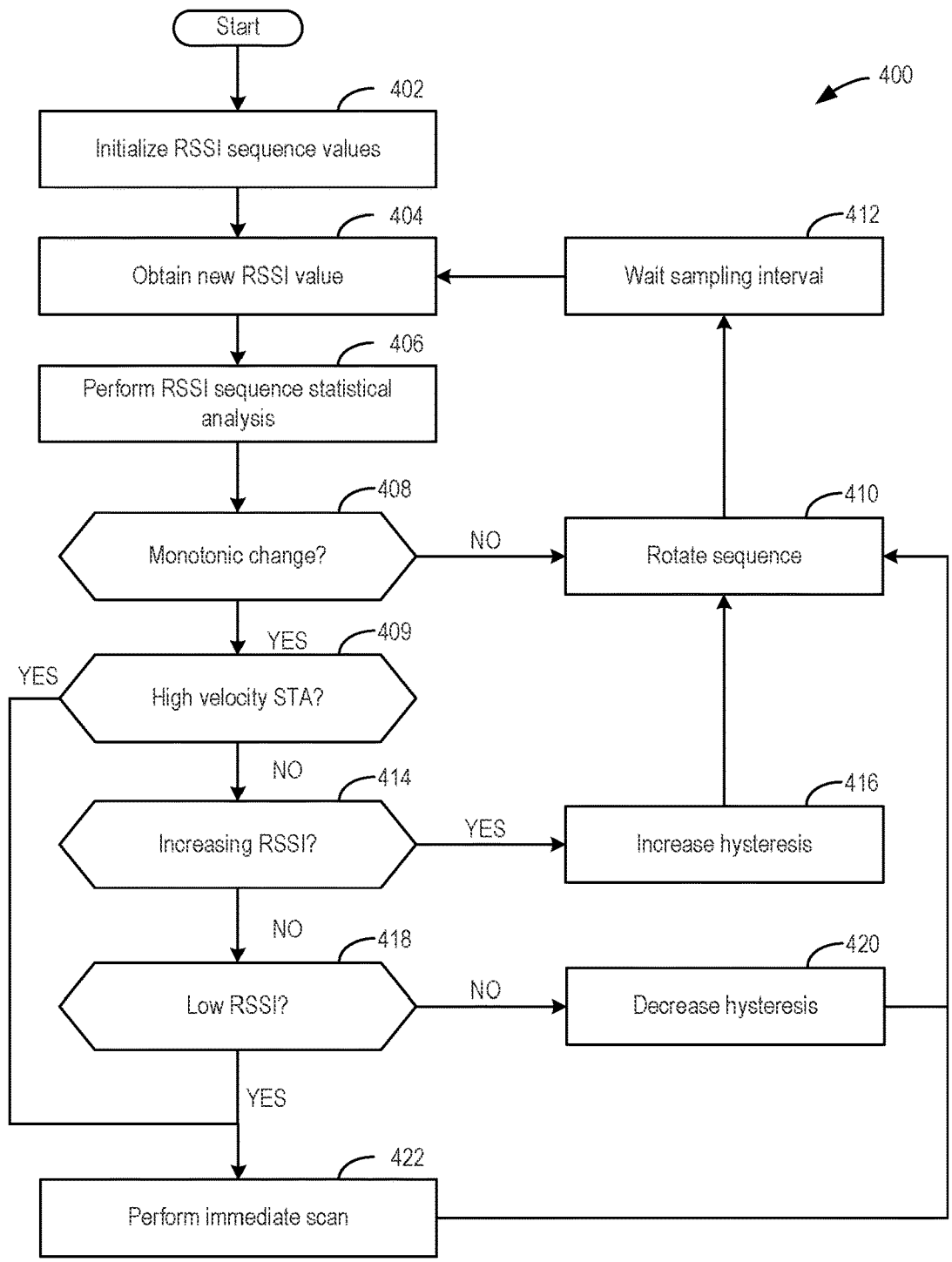
FIG. 4 shows a flow chart illustrating a method for dynamically setting and adjusting a hysteresis value.

The hysteresis value may be a threshold used to determine whether a RSSI of a candidate AP is different enough from the RSSI of an AP connected to the patient monitor. The hysteresis value may be adjusted to allow more or less aggressive roaming of the patient monitor, as further described herein. The method may decrease roaming delay as defined in FIG. 1. The hysteresis value may be adjusted based on a comparison of RSSI rate of change for a first AP and a second AP, as shown in FIG. 3. While FIG. 3 shows two APs, the RSSI rate of change for more than two APs may be compared to adjust the hysteresis value. FIG. 4 illustrates a method for dynamically setting and adjusting a hysteresis value.

When a Wi-Fi STA is in a degraded signal condition or in a highly congested wireless network, it is desirable for the Wi-Fi STA to roam to (e.g., seek out and connect to) a candidate AP with a greater RSSI than an RSSI of the currently connected AP. It is desirable that this is accomplished in a timely manner such that application performance (e.g., monitoring of a patient's physiological information) is not degraded.

A roaming process may include four main categories: trigger, scan, select, and roam. In the trigger phase, the Wi-Fi STA measures a wireless environment it is positioned in and compares measured data to defined trigger thresholds, as further described herein. For example, the Wi-Fi STA measures an RSSI of the currently connected AP to determine if the RSSI is less than an RSSI threshold. Once a trigger threshold is exceeded, the Wi-Fi STA enters the scan phase where it determines what APs are available in the wireless network. Upon completion, the Wi-Fi STA enters the select phase where the Wi-Fi STA determined which of the available APs to connect to. Lastly, the Wi-Fi STA enters the roam phase where the Wi-Fi STA authenticates and associates with a candidate AP, based on AP characteristics described below. All of the above phases are completed prior to the Wi-Fi STA being able to send its intended application data to the network via the connected AP.

Of the four areas above, and assuming that the trigger thresholds are established correctly, roaming delay may occur in the scan phase followed by the roam phase, depending on the complexity of the security method used in the Wi-Fi STA. Roaming delay, or an interruption in application data, is defined as the duration between the last data packet transmitted to the AP the Wi-Fi STA was previously connected to and the first data packet transmitted to the next AP. Roaming delay may increase a roaming response time, increase data loss, and increase power draw due to excessive scanning.

Figure 1:
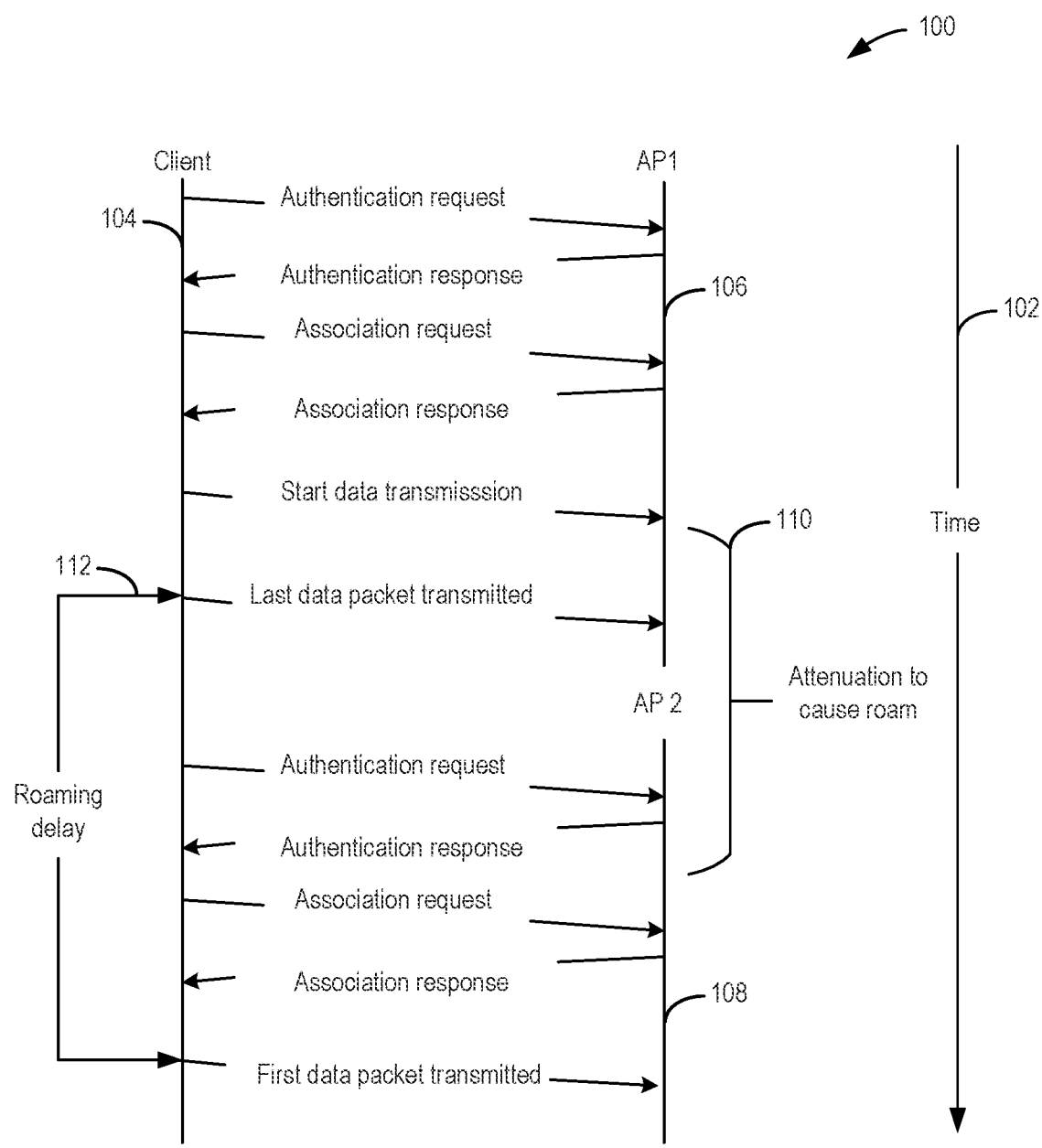
FIG. 1 shows a timeline illustration of roaming delay for a client.

FIG. 1 shows a timeline illustration 100 of roaming delay for a client. Time increases as shown by arrow 102. The client 104 may be a patient monitor, Wi-Fi STA, or other mobile monitoring device which may be wirelessly connected to a network via an AP. The client 104 is initially connected to a first AP (AP1) 106. During the roam phase, the client 104 sends an authentication request to the AP1 106, and the AP1 106 sends an authentication response to the client 104. The client 104 then sends an association request to the AP1 106, and the AP1 106 sends an association response to the client 104. In response to the association response from the AP1 106, the client 104 starts data transmission to the AP1 106. Transmitted data may include patient physiological information such as heart rate, blood pressure, and so on.

It may be desired for the client 104 to roam to a different AP, for example, a second AP (AP2) 108. The client 104 may roam to the AP2 108 when a trigger threshold is exceeded, as briefly described above and further elaborated on below. In the example of FIG. 1, roaming is triggered by a loss of signal strength or by a degradation of signal strength below the trigger threshold in a networking connection, for example, the wireless connection between the client 104 and the AP1 106.

The client 104 sends an authentication request to the AP2 108, and the AP2 108 sends an authentication response to the client 104. A first duration 110 may be a time in which attenuation occurs, thus causing the client 104 to roam. In the example of FIG. 1, the first duration 110 is between the start of data transmission from the client 104 to the AP1 106 and when the client 104 receives the authentication response from the AP2 108.

As was done when connecting the client 104 to the AP1 104, the client 104 sends an association request to the AP2 108 following receipt of the authentication response. The AP2 108 sends an association response to the client 104, and a first data packet is transmitted from the client 104 to the AP2 108.

A roaming delay 112 is the duration between when the last data packet was transmitted from the client 104 to the AP1 106 and when the first data packet is transmitted from the client 104 to the AP2 108. During the roaming delay 112, data (e.g., patient information) may not be transmitted to an AP and therefore not communicated to the network. Medical providers may thus be unable to monitor patients using information gathered by the client 104 for the duration of the roaming delay 112. A method is desired for reducing a duration of roaming delay and thus reducing data loss during roaming. Roaming delay may be reduced by adjusting at least one of: support for multiple trigger parameters (e.g., RSSI and signal-to-noise ratio (SNR)), pre-emptive scanning, hysteresis, and authentication.

The roaming process for a Wi-Fi STA begins following one or more of its trigger thresholds being exceeded. Depending on how configurable the Wi-Fi STA driver/firmware is, any number of a plurality of parameters may be used. The parameters may include RSSI, SNR, data retries in a given time period, number of expected beacons not received in a given time period, current data rate, and time since last scan. RSSI is the parameter most commonly used, however, in a wireless environment where wireless interference or high client loading is anticipated, additional trigger thresholds may be considered. For example, if the Wi-Fi STA has a high RSSI value, but it is operating on a channel that is being interfered with, the noise floor may be higher than normal and/or the data retries may increase. Therefore, a combination of RSSI, SNR, and data retries may be used to trigger the client to roam in higher interference scenarios as well as low signal conditions.

After one or more trigger thresholds have been exceeded, the Wi-Fi STA may scan available channels (e.g., APs) for the Wi-Fi STA to potentially roam to. Active scanning includes the Wi-Fi STA sending out probe requests (e.g., authentication requests) on the channels it is not currently connected to and listening for a first duration (e.g., 10 to 50 ms) for a probe response (e.g., authentication response) from the AP. Passive scanning includes the Wi-Fi STA listening for beacons from APs in the wireless environment. In one example, one beacon may be emitted by an AP per 100 ms. The Wi-Fi STA may thus listen for beacons for 1.5 times the beacon rate (e.g., 150 ms) so as to not miss a present beacon. Active channel scans may be completed faster than passive channel scans. However, Wi-Fi STAs operating in an 802.11a band may use dynamic frequency selection (DFS) to scan available channels. DFS may reduce interference with radar systems that operate on the same channels. Therefore, passive scans are used on UNII-2 and UNII-Worldwide bands.

In the 802.11b/g (2.4 GHz) band, there are between 11 and 14 channels available for use depending on the domain the Wi-Fi STA is operating in (FCC vs. ETSI). In the 802.11a (5 GHz) band, there are up to 23 channels available. If passive scans are done to completion on all 14 802.11b/g and 23 802.11a channels, with a scan delay of 150 ms per channel, scanning alone could amount to 5.5 seconds. With Wi-Fi6E adding up to 59 additional channels, scanning times will increase.

Once the Wi-Fi STA has completed the scanning process, it selects a new, candidate AP to connect to. The candidate AP may have a greater RSSI and/or a lower SNR compared to the AP the Wi-Fi STA is currently connected to. When multiple APs are available in the wireless network which the Wi-Fi STA may roam to, multiple parameters may be considered to determine which AP to roam to. Parameters may include RSSI, SNR, data retries in a given time period, number of expected beacons not received in a given time period, current data rate, time since last scan, AP client loading, and delta from current AP (e.g., hysteresis).

The above-mentioned parameters are similar to those used as trigger thresholds, with the exception of AP client loading and hysteresis. For example, if only RSSI is used to sort candidate APs and the RSSI of an AP having the highest RSSI of the candidate APs is 2 dB greater than the current AP RSSI level, then roaming to the candidate AP may result in more drawbacks than benefits. For example, roaming to the candidate AP having an RSSI 2 dB greater than the current AP induces interruption of application data transmission and is likely to cause another scanning process, as the 2 dB difference may not be a significant increase in signal strength. The inclusion of additional parameters, such as hysteresis, may help make the scanning and roaming steps more selective. The hysteresis value selection process weighs a desire for connection to an AP with a highest connected data rate of the candidate APs and lowest interruption of application data as is tolerable by the Wi-Fi STA. Table 1 below is intended to guide a designer in selecting a hysteresis value that makes the Wi-Fi STA more aggressive (e.g., less sticky) or less aggressive (e.g., more sticky) when deciding to roam from its current AP.

TABLE 1

Hysteresis Guide

| Factor | More "Sticky" | Less "Sticky" |
| --- | --- | --- |
| # of APs for size of facility | Few | More |
| Mobility of Wi-Fi STA | Low | High |
| Bandwidth Utilization | Small | Large |
| Application persistence request | High | Low |

After completion of the select phase, the Wi-Fi STA proceeds to the roam step. Since the IEEE 802.11 protocol uses "break before make" communication, the Wi-Fi STA first disconnects from the current AP. The Wi-Fi STA then switches to the candidate AP, reauthenticates, reassociates, potentially pulls a new IP address (e.g., for layer three roams), all prior to being able to resume sending application data.

The process for a Wi-Fi STA to determine optimal APs to connect to as described above may result in a slow roaming response, increased data loss and increased power draw due to excessive scanning when the Wi-Fi STA is mobile. In the aforementioned example, infrastructure based methods (e.g., IEEE 802.11k, v) manipulate Wi-Fi STA roaming behavior based on Wi-Fi STA performance from the AP's perspective. However, the AP-based methods may miss near-far scenarios where the AP can hear its neighbors and connected STAs (e.g., can detect RSSI and other characteristics listed above), but the Wi-Fi STA itself may be unable to detect a plurality of candidate APs.

The current wpa_supplicant, used for key negotiation with an authenticator on the network infrastructure, controlling roaming behavior and IEEE 802.11 authentication/association of the wireless driver, supports two methods for detecting available APs. A bgscan simple method scans all pre-programmed channels in an array in the same order when a scan request is initiated. If a mobile STA is not in a location where it can hear an AP on a channel listed in the channel array, the wpa_supplicant will still spend 50-150 ms per channel listening for the transmissions from an AP on that channel. The more channels that a STA cannot hear, the more time the STA may take to find a channel deemed a sufficient roaming candidate. Further complicating matters is the release of new spectrum for Wi-Fi 6E in the 6-7 GHz frequency band which will greatly increase the number of channels the STA has potentially available to scan. Conversely, the bgscan learn method scans all channels observed during a previous scan plus one new frequency that was not previously heard during scanning. This method reduces the channel set to what the STA hears in a given location. However, when the STA moves, a potentially entirely new channel list may be desired to capture APs in the new location. Since bgscan learn scans one new channel in addition to the ones it already knows from the previous location, there would be an increased probability of the STA missing available channels as it moves to the new location as subsequent scans might not scan all available channels before the STA moves past a candidate AP.

Both methods scan for channels based on a static, pre-programmed configuration. In other words, the channel scan list is not updated (e.g., add/remove channels) or reordered dynamically based on changing conditions observed by the STA. Something between the two methods is desired to optimize roaming performance for Wi-Fi STAs that have Wi-Fi PHY/MAC radios reliant on a host processor running an OS as well as self-contained Wi-Fi radios running their own OS.

As briefly described above, FIG. 4 illustrates a method for dynamically setting and adjusting a hysteresis value. The hysteresis value may be increased when an RSSI of the connected AP shows a monotonic change, the STA does not have a high velocity, and the RSSI of the connected AP is increasing. The hysteresis value may be decreased when the RSSI of the connected AP shows a monotonic change, the STA does not have a high velocity, the RSSI of the connected AP is not increasing, and the RSSI of the connected AP is not low. The hysteresis value may be unchanged when either the RSSI of the connected AP does not show a monotonic change or the STA does have a high velocity. Further detail regarding RSSI thresholds is described in FIGS. 3-4. Thus, having the ability to dynamically change the hysteresis value based on changing signal conditions may decrease a roaming delay of the Wi-Fi STA and allow the Wi-Fi STA to roam to an AP with a greater RSSI, thus reducing data loss and reducing power draw during roaming.

A method is disclosed herein for dynamic setting and adjustment of a hysteresis value using information available to the STA. The information used may include a distance from the STA to an AP connected to the STA, combined with a determination of whether the STA is mobile or not and its direction of movement with respect to the connected AP.

In one embodiment, one beacon is broadcast from an AP per 100 ms and the STA records the RSSI of each of a plurality of beacons it receives from a given AP. For example, the RSSI is the signal strength of the beacon as it is received by the STA. In other words, the RSSI is a power level that the STA observes of the received beacon. The STA averages the RSSI level from the received beacons over, for example, 5-10 consecutive samples from the given AP. A sliding window of RSSI rate of change may be used to estimate proximity of the STA to the currently connected AP as well as to candidate APs identified during scanning. Further detail regarding estimation of distance using RSSI rate of change is shown in FIG. 3. RSSI rates of changes between the current AP and candidate APs may be compared to determine generally how close to or far from any given AP a STA is to determine which AP might be the closest to the STA and therefore may have a stronger signal between the STA and the AP when the STA is mobile.

Before further discussion of the method for dynamic setting and adjustment of a hysteresis value, an example system in which the method may be implemented is shown. FIG. 2 shows one embodiment of a schematic block diagram illustrating communication of a patient monitor with a plurality of access points (APs) according to a method for setting and dynamic adjustment of a hysteresis value. A system 200 includes a patient monitor 210 having a WLAN card 220 (e.g., a wireless card) and a transmitter 231. A plurality of APs 250, each having a transceiver 230 are dispersed throughout a physical space, for example, a hospital or other healthcare facility. The plurality of APs 250 are thus dispersed throughout a wireless network and are connected through a network 260.

The patient monitor 210, may be any patient monitoring device with wireless monitoring capabilities. For example, the patient monitor 210 may be a Wi-Fi station (STA). In one embodiment, the WLAN card 220 is an original equipment manufacturer (OEM) card and includes a storage medium having computer executable code and a processor to execute the code. The WLAN card 220 may thus implement the method for setting and dynamically adjusting the hysteresis value, as further described herein. In further embodiments, the patient monitor 210 includes a storage medium and a processor which are not part of the WLAN card 220 and operate to store and execute computer executable code, respectively. Additional embodiments of the system 200 may include a patient monitor 210 without a WLAN card 220 and the patient monitor 210 may have hardwired circuitry and executable code incorporated directly therein.

The patient monitor 210 communicates with the plurality of APs 250 via a wireless transmission 240, wherein the wireless transmission 240 couples the patient monitor 210 and at least one of the plurality of APs 250 through a respective transceiver 230 of each of the patient monitor 210 and the plurality of APs 250. The plurality of APs 250 are connected through the network 260. For example, the system 200 may include n number of APs 250 connected to the network 260. The plurality of APs 250 may be configured throughout the area of the system 200 to monitor a number of patient monitors 210, which are also configured throughout the system 200 and being placed in proximity to a patient being monitored. In the herein described example, the system 200 is a wireless system and patient monitors within the system 200 may be mobile. The network 260 receives wirelessly transmitted information from the APs 250 and relays the information collected from the APs 250 to a hospital information system suitable for collecting and managing such information. Such hospital information systems are known in the art and the present system 200 is adaptable to different hospital information systems.

In operation, the system 200 includes the patient monitor 210 which is in communication through the wireless transmission 240 to a first one of the plurality of APs 250. Physiological information collected by the patient monitor 210 is relayed through the first AP to the network 260. The system 200 uses the WLAN card 220 and the transceivers 230 associated with the patient monitor 210 and APs 250 to facilitate wireless transmission 240 of the physiological data.

Once the patient monitor 210 is in wireless transmission 240 with the first AP, the WLAN card 220 conducts a scan of the system 200 to determine if another of the APs 250 may have a stronger signal quality than the first AP the patient monitor 210 is currently in communication with. As described above, current system may use the signal strength of access points 250 to determine whether to enter a roaming mode, thus allowing the patient monitor 210 to connect with a second access point and drop the first access point. However, in the system 200 of the present application, deciding which AP to connect to is done by comparing RSSIs of each of the APs 250, a relative distance from the Wi-Fi STA to each of the plurality of APs 250, movement of the Wi-Fi STA relative to each of the plurality of APs 250, and a hysteresis value.

In one embodiment, a signal quality of the first AP that is currently connected with the patient monitor 210 is compared to a signal quality of each of the plurality of APs 250 determined during a scan of the wireless network. If the signal quality of the first AP is greater than those collected from the scan, then the system waits a predetermined amount of time before conducting another scan. If, however, signal quality of the first AP is less than any of the signal qualities of the plurality of APs 250, then the WLAN card 220 enters a roaming mode to connect to a second AP having a stronger signal quality relative to the first AP. The method is repeated when a trigger threshold is exceeded, as described above, as the Wi-Fi STA is mobile. The method is further elaborated on in FIGS. 4-5.

Prior to discussion of the method for dynamically setting and adjusting the hysteresis value, and roaming to a candidate AP of the plurality of APs, a graph 300 is shown in FIG. 3 for determining a relative distance from the Wi-Fi STA to two APs of a wireless network. RSSI in dBm is shown on the y-axis and time is shown on the x-axis, with time markers of interest t1-t3. While graph 300 shows two APs, the method described herein may be applied to a wireless system with n number of APs.

Beacons may be broadcast from each AP of a plurality of APs within a wireless network (e.g., system 200 of FIG. 2), and a Wi-Fi STA within the wireless network records the RSSI of each received beacon from a given AP. A WLAN chip or other processor of the Wi-Fi STA may then employ averaging of the RSSI levels for each AP over a first sample set (e.g., 5-10 consecutive samples) to generate a plot showing RSSI change over time.

When a Wi-Fi STA moves away from an AP, the RSSI value degrades over time where the degradation typically follows a logarithmic curve. In other words, the RSSI initially degrades quickly and then the degradation flattens out the further the Wi-Fi STA moves away from a given AP. A first plot 302 shows an RSSI value of a first AP over time. The first AP may be connected to the Wi-Fi STA initially (e.g., prior to t1). The first plot 302 shows logarithmic degradation of the RSSI signal, indicating the Wi-Fi STA may be moving away from the first AP. A second plot 304 shows an RSSI value of a second AP over time, where the second AP may not be connected to the Wi-Fi STA prior to t1. The second plot shows logarithmic growth over time, indicating the Wi-Fi STA may be moving towards the second AP. At time t2, the Wi-Fi STA may be equidistant from the first AP and the second AP.

An RSSI rate of change for each of the two APs may be used to determine a distance as well as direction of movement of the Wi-Fi STA relative to the respective AP. A rapid rate of change may indicate that the Wi-Fi STA is close to a given AP whereas a slow rate of change could indicate the STA is far away from a given AP. For example, a RSSI rate of change of −20 dB per 10 beacons could indicate that the Wi-Fi STA is close to a given AP and possibly moving away from the given AP. A rate of change of −5 dB per 10 beacons may indicate the Wi-Fi STA is far from the given AP and possibly moving away from the given AP. It may be determined if the rate of change is rapid or slow based on an upper threshold and a lower threshold. For example, the upper threshold may be −20 dB per 10 beacons and when the rate of change is greater than or equal to −20 dB, the rate of change may be considered high or rapid. The lower threshold may be −5 dB and, when the rate of change is less than or equal to the lower threshold, the rate of change may be considered slow.

Multiple subsequent RSSI rate of change declines or increases for a given AP would further strengthen direction of movement. For example, an RSSI rate of change of −20 dB, followed by −10 dB and then −5 dB per 10 beacons would indicate the STA is continuously moving away from a given AP, whereas the opposite (e.g., +5 dB, +10 dB, +20 dB) would indicate movement towards an AP.

When multiple RSSI rates of change are compared, for example, during multiple periods for a given AP or during the same period for multiple APs, relative distance from the Wi-Fi STA may be determined. In one example, when a first RSSI rate of change is slower than a second RSSI rate of change, an AP having the first RSSI rate of change may be further from the Wi-Fi STA than an AP having the second rate of change. During a first period 306, an RSSI rate of change for the first AP shown by plot 302 may be greater than an RSSI rate of change for the second AP shown by plot 304 during a second period 308. Thus, a distance between the Wi-Fi STA and the first AP may be less than a distance between the Wi-Fi STA and the second AP, and the Wi-Fi STA may be moving away from the first AP and towards the second AP.

Roaming parameters that influence how aggressive the Wi-Fi STA is when determining when to roam may be modified accordingly based on the RSSI rate of change and implied directionality from a given AP. For example, a hysteresis value used to determine a threshold value (e.g., signal strength) for roaming from the current AP (e.g., the first AP) to a candidate AP (e.g., the second AP) could be set to a large value when stationary to avoid flip-flopping (e.g., rapidly roaming back and forth) between two APs of similar RSSI. Alternatively, the hysteresis value could be adjusted to a lower value when mobile to allow the STA to be more aggressive in roaming to a new AP that it is headed toward. Furthermore, if the STA was far away from any candidate APs, the hysteresis value could be adjusted even lower to allow the STA to connect to any candidate AP that with a slightly higher signal strength to increase the probability of not losing connection entirely.

The hysteresis value may further be adjusted with a first adjustment factor proportional to an RSSI rate of change when the RSSI rate of change is increasing, and adjusted with a second adjustment factor proportional to the RSSI rate of change when the RSSI rate of change is decreasing. The second adjustment factor may be greater than the first adjustment factor, such that, when the second adjustment factor is implemented, the hysteresis value may be adjusted more than when the first adjustment factor is implemented. Adjustment of the hysteresis value using the second adjustment factor may thus allow for more selective roaming of the Wi-Fi STA to a candidate AP when the Wi-Fi STA is far from the candidate AP and/or far from the currently connected AP.

In the example of FIG. 3, the hysteresis value may be high prior to t1. The high hysteresis value may be 8 dB and may be initially set as determined by manufacturers of the WLAN chip or during configuration of the wireless network, for example. At time t1, the hysteresis value may be adjusted to a low hysteresis value (e.g., relative to the hysteresis value prior to t1). The hysteresis value may be low between t1 and t3 due to the Wi-Fi STA being mobile and, given the Wi-Fi STA is equidistant from the first AP and the second AP at time t2, may allow the Wi-Fi STA to be more selective when deciding whether to roam to the second AP or remain connected to the first AP. For example, as the first AP and the second AP have similar RSSI values between t1 and t2, the low hysteresis value may allow the Wi-Fi STA to roam to the AP which it is moving towards (e.g., the second AP). At t3, the hysteresis value may be adjusted to be high, for example, higher than the hysteresis value between t1 and t3. As the first plot 302 and the second plot 304 diverge following t2, the high hysteresis value may allow the Wi-Fi STA to roam to the second AP. The hysteresis value may be adjusted based on factors including a number of APs within the wireless network, mobility of the Wi-Fi STA, bandwidth utilization, application persistence request, distance between the Wi-Fi STA and the plurality of APs, and so on). Further detail regarding adjustment of the hysteresis value is described in FIG. 4.

As briefly described in FIG. 3, the hysteresis value may be adjusted to control roaming of the Wi-Fi STA while the Wi-Fi STA is mobile and/or when the Wi-Fi STA is stationary and the surrounding environment is changing. FIG. 4 shows a flow chart illustrating a method 400 for dynamically setting and adjusting a hysteresis value. The method 400 includes steps for Wi-Fi STA roaming based AP information available to the Wi-Fi STA. The method 400 may be implemented when a trigger threshold, as described above, is exceeded, and the Wi-Fi STA enters the scan phase. In some embodiments, method 400 may be executed by the WLAN card 220 of the patient monitor 210 of FIG. 2. The method described herein is described with reference to the wireless network system of FIG. 2, and may be applied to other embodiments of wireless network systems including at least two APs and a mobile patient monitoring device.

At step 402, the method 400 includes initializing RSSI sequence values, which may include determining RSSI values of a connected AP (e.g., an AP currently connected to the Wi-Fi STA). When the Wi-Fi STA is mobile or a surrounding environment is changing, a signal strength between the Wi-Fi STA and the connected AP may change, as indicated by the RSSI values.

At step 404, method 400 includes obtaining a new RSSI value. The new RSSI value may be from the connected AP and be assigned an 'n' RSSI value. Each of the plurality of APs may broadcast a beacon at a frequency of one beacon per 100 ms, in one example. The beacons may include information about the respective AP, including an RSSI value. The Wi-Fi STA may receive a beacon from the connected AP and record the RSSI of the received beacon. The RSSI of each received beacon may be compiled on a list of RSSI values stored on an external device, such as the WLAN card 220 of FIG. 2. Step 404 may obtain the 'n' RSSI value by identifying the most recent RSSI on the list of RSSI values.

At step 406, the method 400 includes performing RSSI sequence statistical analysis. This may include averaging the RSSI value from received beacons over a first duration for the connected AP. For example, the Wi-Fi STA may average the RSSI values of ten consecutively received beacons for the connected AP. In another example, the first duration may be a different number of beacons, such as between five and ten beacons. The method 400 may further include averaging RSSI values of received beacons over multiple durations. For example, the RSSI values of ten consecutively received beacons for the connected AP are averaged, as described above. The next ten consecutively received beacons for the connected AP may then be averaged, and so on. In another example, a sliding window may be used to average RSSI values of the connected AP. The RSSI values of a first through a tenth beacon may be averaged to give a first average RSSI. After obtaining an eleventh beacon (e.g., the 'n' RSSI value obtained at step 404), the RSSI values of a second through the eleventh beacon may be averaged to give a second average RSSI, and so on as more beacons are obtained.

Performing RSSI sequence statistical analysis may further include determining an RSSI rate of change to estimate a relative proximity of the connected AP to the Wi-Fi STA. The RSSI rate of change may be calculated from a plurality of averaged RSSI values, as described in step 406. A visual representation of the RSSI rate of change for a first AP (e.g., the connected AP) and a second AP (e.g., a candidate AP) is shown on the graph 300 of FIG. 3. The RSSI rate of change of the connected AP may be determined, for example, during the first period 306 of FIG. 3 for the first AP.

Once the RSSI rate of change is determined for the connected AP, at step 408, method 400 includes determining if a monotonic change occurs in the RSSI value over time plot, as shown in FIG. 3. If a monotonic change does not occur, that is, a plot of the RSSI value over time is equal to a first RSSI value for the duration of the period, it may be determined that a signal strength between the Wi-Fi STA and the connected AP is not changing. Thus, the Wi-Fi STA may be stationary (e.g., not moving towards or away from the connected AP) and/or the environment is not changing or is changing in a way that may not affect the signal strength between the Wi-Fi STA and the connected AP.

If there is no monotonic change at step 408, the method 400 proceeds to step 410 to rotate a sequence. Rotating the sequence may include changing a position of RSSI values in the list of RSSI values stored on the external device. For example, the 'n' RSSI value may be moved from the 'n' position in the sequence to an 'n−1' position, such that a new RSSI value obtained from a beacon may be assigned as the 'n' RSSI value. The method 400 proceeds to step 412, where the method 400 includes waiting a sampling interval before receiving the new RSSI value at step 404. In one example, the sampling interval may be 30 seconds.

Returning to step 408, if the RSSI value over time plot includes a monotonic change, the method 400 proceeds to step 409. For example, the monotonic change may include a monotonic increase or decrease of the RSSI value, such that the RSSI value is either increasing or decreasing, and not initially increasing then decreasing, or vice-versa.

At step 409, the method 400 includes determining if the Wi-Fi STA has a high velocity. A velocity of the Wi-Fi STA (e.g., a speed at which the Wi-Fi STA is moving towards or moving away from the connected AP) may be determined based on the RSSI rate of change calculated at step 406. If the RSSI rate of change is greater than a first threshold rate of change, it may be determined that the Wi-Fi STA is moving at a high velocity towards or away from the connected AP. If the Wi-Fi STA is moving at a high velocity, for example a velocity greater than or equal to a threshold velocity, the method 400 may proceed to step 422 to perform an immediate scan, as further described below. If it is determined that the Wi-Fi STA is not moving at a high velocity (e.g., less than the threshold velocity), the method 400 may proceed to step 414.

At step 414, the method 400 includes determining if the RSSI value is increasing. The RSSI value may be increasing when the Wi-Fi STA is moving towards the connected AP, such that a distance between the connected AP and the Wi-Fi STA is decreasing. The RSSI value may be decreasing when the Wi-Fi STA is moving away from the connected AP, such that a distance between the connected AP and the Wi-Fi STA is increasing. Additionally or alternatively, the RSSI value may be decreasing when the environment is changing, such as a door closing between the connected AP and the Wi-Fi STA. The RSSI value may not be increasing or decreasing if the Wi-Fi STA is stationary and/or the environment is unchanged.

If the RSSI is not increasing (e.g., decreasing or remaining unchanged), at step 416, the method 400 includes increasing a hysteresis value. As the hysteresis value is a threshold RSSI value used to control whether the Wi-Fi STA may roam to a candidate AP from the connected AP, increasing the hysteresis value may allow the Wi-Fi STA to be less selective when roaming. In one example, the hysteresis value may be increased from 2 dB to 10 dB, such that the Wi-Fi STA may not switch from the connected AP to the candidate AP when the candidate AP RSSI is less than 10 dB greater than the RSSI of the connected AP. Instead, the Wi-Fi STA may switch from the connected AP to the candidate AP when the candidate AP RSSI is at least 10 dB greater than the RSSI of the connected AP. The method 400 proceeds to step 410 to rotate the sequence and wait the sampling interval before receiving a new RSSI value, as described above.

If the RSSI is increasing at step 414, at step 418, the method 400 includes determining if the RSSI of the connected AP is low. The RSSI may be considered low when the RSSI value is less than a threshold RSSI value. The threshold RSSI value may be −65 dBm. The RSSI of the connected AP may be low when the Wi-Fi STA far from the connected AP.

If at step 414 it is determined that the RSSI is not low, at step 420, the method 400 includes decreasing the hysteresis value. Decreasing the hysteresis value may allow the Wi-Fi STA to be more selective when roaming. For example, the hysteresis value may be decreased from 10 dB to 2 dB, such that the Wi-Fi STA may switch from the connected AP to the candidate AP when the candidate AP RSSI is within 2 dB of the connected AP RSSI. This may allow the Wi-Fi STA to roam to an AP with a higher RSSI, and thus stronger signal, when the Wi-Fi STA is far from the connected AP and the candidate AP. The method 400 then proceeds to step 410 to rotate the sequence and wait the sampling interval before receiving a new RSSI value at step 404.

Returning to step 418, if the RSSI is low the method 400 includes performing an immediate scan at step 422. Performing the immediate scan may include scanning the wireless network system for beacons to determine the RSSI values of APs other than the connected AP in the wireless network. In this example, the RSSI value of the connected AP may be greater, and therefore stronger than the RSSI value of other APs in the wireless network system. The method 400 may return to step 410 to rotate the sequence, wait the sampling interval at step 412, and receive a new RSSI value at step 404. In this way, the method 400 may allow the Wi-Fi STA to continuously monitor RSSI values of the connected AP, determine if a hysteresis value adjustment is requested, and dynamically adjust the hysteresis value accordingly. The Wi-Fi STA may thus be able to connect to a candidate AP of the wireless network system with a strong signal as the Wi-Fi STA is mobile throughout an area covered by the wireless network system, allowing rapid, continuous transmission of patient data to the network such that the data may be used by medical personnel for patient care.

The technical effect of dynamically setting and adjusting a hysteresis value of a mobile patient monitor is a decrease in roaming delay, reduced data loss, and reduced power draw during roaming of the mobile patient monitor.

The disclosure also provides support for a method for a wireless monitoring system, comprising: roaming to an access point (AP) based on a received signal strength indicator (RSSI) of a candidate AP relative to a hysteresis threshold and, adjusting the hysteresis threshold responsive to a rate of change of an RSSI of a connected AP. In a first example of the method, the wireless monitoring system is of a medical device. In a second example of the method, optionally including the first example, the wireless monitoring system is a mobile system. In a third example of the method, optionally including one or both of the first and second examples, the RSSI of the connected AP and the RSSI of the candidate AP is measured by the wireless monitoring system. In a fourth example of the method, optionally including one or more or each of the first through third examples, the hysteresis threshold is adjusted based on a direction of the rate of change of the RSSI of the connected AP and a velocity of the wireless monitoring system. In a fifth example of the method, optionally including one or more or each of the first through fourth examples, the method further comprises: determining a distance of the connected AP from the wireless monitoring system, and wherein adjusting the hysteresis threshold responsive to the rate of change of the RSSI includes adjusting the hysteresis threshold based on a rate of change of the distance. In a sixth example of the method, optionally including one or more or each of the first through fifth examples, the velocity of the wireless monitoring system is determined using the rate of change of the RSSI of the connected AP. In a seventh example of the method, optionally including one or more or each of the first through sixth examples, the hysteresis threshold is increased when the RSSI shows a monotonic change, the velocity of the wireless monitoring system is lower than a lower threshold, and the RSSI is increasing. In an eighth example of the method, optionally including one or more or each of the first through seventh examples, the hysteresis threshold is decreased when the RSSI shows a monotonic change, the velocity of the wireless monitoring system is lower than a lower threshold, the RSSI is decreasing, and the RSSI of the connected AP is higher than an upper threshold. In a ninth example of the method, optionally including one or more or each of the first through eighth examples, the hysteresis threshold is unchanged when either the RSSI of the connected AP does not show a monotonic change or the velocity of the wireless monitoring system is higher than an upper threshold, or when the RSSI shows a monotonic change, the velocity of the wireless monitoring system is lower than a lower threshold, the RSSI is decreasing, and the RSSI of the connected AP is lower than the lower threshold. In a tenth example of the method, optionally including one or more or each of the first through ninth examples, the candidate AP is roamed to when a difference between the RSSI of the candidate AP and the RSSI of the connected AP is greater than or equal to the hysteresis threshold.

The disclosure also provides support for a wireless network system, comprising: a network, a plurality of access points (APs) in wireless communication with the network, and a Wi-Fi station (STA) in wireless communication with at least one of the plurality of APs, the Wi-Fi STA configured with computer-readable instructions that when executed cause the Wi-Fi STA to: adjust a hysteresis threshold responsive to a rate of change of a received signal strength indicator (RSSI) of an AP in wireless communication with the Wi-Fi STA. In a first example of the system, the computer-readable instructions are stored on a storage medium of a WLAN card and executed by a processor of the WLAN card. In a second example of the system, optionally including the first example, the Wi-Fi STA is of a mobile medical device. In a third example of the system, optionally including one or both of the first and second examples, each of the plurality of APs broadcasts a beacon at a first frequency, and wherein each of a plurality of beacons broadcast by each of the plurality of APs are received by the STA and recorded as an RSSI value of a respective AP. In a fourth example of the system, optionally including one or more or each of the first through third examples, the RSSI of the AP in wireless communication with the Wi-Fi STA is measured by the Wi-Fi STA. In a fifth example of the system, optionally including one or more or each of the first through fourth examples, adjusting the hysteresis threshold includes performing RSSI sequence statistical analysis to determine an RSSI rate of change, a velocity of the Wi-Fi STA, and a direction of the RSSI rate of change, and adjusting the hysteresis threshold based thereon.

The disclosure also provides support for a method for a wireless monitoring system, comprising: initializing a plurality of received signal strength indicator (RSSI) signal values of an access point (AP) in wireless communication with the wireless monitoring system, obtaining an observed RSSI value observed by a Wi-Fi station (STA), performing RSSI sequence statistical analysis to determine an RSSI rate of change, a velocity of the wireless monitoring system, and a direction of the RSSI rate of change, and adjusting a hysteresis value based on the RSSI rate of change, the velocity, and the direction of the RSSI rate of change. In a first example of the method, the method further comprises: increasing the hysteresis value when the RSSI shows a monotonic change, the velocity is below a first threshold, and the RSSI is increasing. In a second example of the method, optionally including the first example, the method further comprises: decreasing the hysteresis value when the RSSI shows a monotonic change, the velocity is below a first threshold, the RSSI is decreasing, and the observed RSSI value greater than or equal to a lower threshold.

As used herein, an element or step recited in the singular and preceded with the word "a" or "an" should be understood as not excluding plural of said elements or steps, unless such exclusion is explicitly stated. Furthermore, references to "one embodiment" of the present disclosure are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the method and systems, including the best mode, and also to enable a person of ordinary skill in the relevant art to practice the method and systems, including making and using any devices or systems and performing any incorporated methods. The patentable scope of the disclosure is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for a wireless monitoring system, comprising:
    roaming to an access point (AP) based on a received signal strength indicator (RSSI) of a candidate AP relative to a hysteresis threshold;
    adjusting the hysteresis threshold responsive to a rate of change of an RSSI of a connected AP, the hysteresis threshold adjusted based on a direction of the rate of change of the RSSI of the connected AP and a velocity of the wireless monitoring system; and
    determining a distance of the connected AP from the wireless monitoring system, wherein adjusting the hysteresis threshold responsive to the rate of change of the RSSI of the connected AP includes adjusting the hysteresis threshold based on a rate of change of the distance.

2. The method of claim 1, wherein the wireless monitoring system is of a medical device.

3. The method of claim 2, wherein the wireless monitoring system is a mobile system.

4. The method of claim 1, wherein the RSSI of the connected AP and the RSSI of the candidate AP is measured by the wireless monitoring system.

5. The method of claim 1, wherein the velocity of the wireless monitoring system is determined using the rate of change of the RSSI of the connected AP.

6. The method of claim 1, wherein the hysteresis threshold is increased when the RSSI of the connected AP shows a monotonic change, the velocity of the wireless monitoring system is lower than a lower threshold, and the RSSI of the connected AP is increasing.

7. The method of claim 1, wherein the hysteresis threshold is decreased when the RSSI of the connected AP shows a monotonic change, the velocity of the wireless monitoring system is lower than a lower threshold, the RSSI of the connected AP is decreasing, and the RSSI of the connected AP is higher than an upper threshold.

8. The method of claim 1, wherein the hysteresis threshold is unchanged when either the RSSI of the connected AP does not show a monotonic change or the velocity of the wireless monitoring system is higher than an upper threshold, or when the RSSI of the connected AP shows a monotonic change, the velocity of the wireless monitoring system is lower than a lower threshold, the RSSI of the connected AP is decreasing, and the RSSI of the connected AP is lower than the lower threshold.

9. The method of claim 1, wherein the candidate AP is roamed to when a difference between the RSSI of the candidate AP and the RSSI of the connected AP is greater than or equal to the hysteresis threshold.

10. A wireless network system, comprising:
    a network;
    a plurality of access points (APs) in wireless communication with the network; and
    a Wi-Fi station (STA) in wireless communication with at least one of the plurality of APs, the Wi-Fi STA configured with computer-readable instructions that when executed cause the Wi-Fi STA to:
        adjust a hysteresis threshold responsive to a rate of change of a received signal strength indicator (RSSI) of an AP of the plurality of APs in wireless communication with the Wi-Fi STA, wherein the hysteresis threshold is adjusted based on a direction of the rate of change of the RSSI of the connected AP and a velocity of the wireless monitoring system, and wherein the velocity of the wireless monitoring system is determined using the rate of change of the RSSI of the connected AP.

11. The wireless network system of claim 10, wherein the computer-readable instructions are stored on a storage medium of a WLAN card and executed by a processor of the WLAN card.

12. The wireless network system of claim 10, wherein the Wi-Fi STA is of a mobile medical device.

13. The wireless network system of claim 10, wherein each of the plurality of APs broadcasts a beacon at a first frequency, and wherein each of a plurality of beacons broadcast by each of the plurality of APs is received by the STA and recorded as an RSSI value of a respective AP.

14. The wireless network system of claim 10, wherein the RSSI of the AP in wireless communication with the Wi-Fi STA is measured by the Wi-Fi STA.

15. The wireless network system of claim 11, wherein adjusting the hysteresis threshold includes performing RSSI sequence statistical analysis to determine an RSSI rate of change of the AP, a velocity of the Wi-Fi STA, and a direction of the RSSI rate of change, and adjusting the hysteresis threshold based on the direction of the RSSI rate of change.

16. A method for a wireless monitoring system, comprising:
    initializing a plurality of received signal strength indicator (RSSI) signal values of an access point (AP) in wireless communication with the wireless monitoring system;
    obtaining an observed RSSI value observed by a Wi-Fi station (STA) of the plurality of the RSSI signal values;
    performing RSSI sequence statistical analysis to determine an RSSI rate of change of the plurality of RSSI signal values of the AP, a velocity of the wireless monitoring system, and a direction of the RSSI rate of change; and
    adjusting a hysteresis value based on the RSSI rate of change, the velocity, and the direction of the RSSI rate of change.

17. The method of claim 16, further comprising increasing the hysteresis value when the RSSI rate of change shows a monotonic change, the velocity is below a first threshold, and the RSSI rate of change is increasing.

18. The method of claim 16, further comprising decreasing the hysteresis value when the RSSI rate of change shows a monotonic change, the velocity is below a first threshold, the RSSI rate of change is decreasing, and the observed RSSI value greater than or equal to a lower threshold.

* * * * *